(12) United States Patent
Riddoch et al.

(10) Patent No.: US 11,996,209 B2
(45) Date of Patent: May 28, 2024

(54) 82RB ELUTION SYSTEM AND DOSE CALIBRATOR CONFIGURATIONS

(71) Applicant: JUBILANT DRAXIMAGE INC., Kirkland (CA)

(72) Inventors: Robert William Riddoch, Quebec (CA); Etienne Lefort, Quebec (CA); Paul Donnelly, Quebec (CA); Riccardo Santopietro, Quebec (CA); Thomas Allen Moore, Quebec (CA)

(73) Assignee: Jubilant Draximage Inc., Kirkland (CA)

( * ) Notice: Subject to any disclaimer, the term of this patent is extended or adjusted under 35 U.S.C. 154(b) by 768 days.

(21) Appl. No.: 17/269,588

(22) PCT Filed: Aug. 22, 2019

(86) PCT No.: PCT/US2019/047687
§ 371 (c)(1),
(2) Date: Feb. 19, 2021

(87) PCT Pub. No.: WO2020/041578
PCT Pub. Date: Feb. 27, 2020

(65) Prior Publication Data
US 2021/0313084 A1 Oct. 7, 2021

Related U.S. Application Data

(60) Provisional application No. 62/721,042, filed on Aug. 22, 2018.

(51) Int. Cl.
*G21G 1/00* (2006.01)
*A61M 5/142* (2006.01)

(52) U.S. Cl.
CPC ........... *G21G 1/0005* (2013.01); *A61M 5/142* (2013.01); *G21G 1/001* (2013.01); *A61M 2205/70* (2013.01); *G21G 2001/0031* (2013.01)

(58) Field of Classification Search
CPC ................. G21G 1/0005; G21G 1/001; G21G 2001/0031; A61M 5/142; A61M 2205/70;
(Continued)

(56) References Cited

U.S. PATENT DOCUMENTS 4,585,009 A 4/1986 Barker et al.
8,295,916 B2 10/2012 Shimchuk et al.
(Continued)

FOREIGN PATENT DOCUMENTS

WO 2016/086219 A1 6/2016
WO 2018/057636 A1 3/2018

*Primary Examiner* — Huy Tram Nguyen
(74) *Attorney, Agent, or Firm* — BakerHostetler (57) ABSTRACT

Disclosed herein are rubidium elution systems comprising a primary assembly including a $^{82}Sr/^{82}Rb$ generator, an activity detector, a waste container, a pump system, a sensor, a tubing circuit, at least one valve, and a computer; and a dose calibrator outside the primary assembly. The system may have an interface for configuring the dose calibrator, and a locking means for preventing access to the interface and reconfigurations of its parameters. Moreover, the dose calibrator may be in electronic communication with the computer of the system. Furthermore, the electronic communication can be embodied with an electronic cable having a breakaway connector. Also, the dose calibrator may be positioned on a mobile platform.

21 Claims, 5 Drawing Sheets

(58) Field of Classification Search
CPC .... A61M 2039/1061; A61M 2205/276; B62B 3/008; B62B 2207/00
USPC ...................................................... 422/159
See application file for complete search history.

(56) References Cited

U.S. PATENT DOCUMENTS

| | | |
|---|---|---|
| 9,299,468 B2 | 3/2016 | Hidem et al. |
| 2007/0228680 A1 | 10/2007 | Reppert et al. |
| 2008/0177126 A1 | 7/2008 | Tate et al. |
| 2009/0312635 A1 | 12/2009 | Shimchuk et al. |
| 2015/0228368 A1 | 8/2015 | Lefort et al. |
| 2015/0357753 A1 | 12/2015 | Lee |

$^{82}$RB ELUTION SYSTEM AND DOSE CALIBRATOR CONFIGURATIONS

CROSS-REFERENCE TO RELATED APPLICATIONS

This application is the National Stage Application of International Patent Application No. PCT/US2019/047687 filed Aug. 22, 2019, which claims the benefit of priority to U.S. Provisional Application No. 62/721,042, filed Aug. 22, 2018, the entire contents of both of which are incorporated herein by reference.

TECHNICAL FIELD

The present disclosure generally relates to nuclear medicine, and specifically concerns mobile $^{82}$Sr/$^{82}$Rb elution system.

BACKGROUND

The subject matter disclosed herein relates to radiopharmaceutical substances with a short half-life like Rubidium ($^{82}$Rb). Rubidium ($^{82}$Rb) is used as a positron emission tomography (PET) tracer for non-invasive determination of myocardial perfusion (blood flow).

$^{82}$Sr/$^{82}$Rb elution systems typically comprise a reservoir of sterile saline solution (e.g. 0.9% Sodium Chloride Injection), a pump system to push the sterile saline solution from a reservoir, a source for generating radioactive isotopes in solution, a radioactivity detector to measure activity of different isotopes, a dose calibrator, a waste container, a set of infusion tubing assembly, one or more sensors, a computer, and shielded enclosures on a platform for transporting the elution system. During operation, the pump moves saline solution from the reservoir and through the generator in order to elute the $^{82}$Rb in the form of $^{82}$RbCl, and also to regulate the flow of sterile saline solution to a bypass line. The radioactive solution which comes out from the generator is then infused to a patient to be diagnosed via a patient outlet. As known in the art, $^{82}$Rb is generated by radioactive decay of $^{82}$Sr, and thus the rate of production of $^{82}$Rb at any given time is a function of the activity of $^{82}$Sr remaining in the generator. The rate of $^{82}$Rb production exponentially decreases through the useful life of the generator, in direct correlation with the half-life of $^{82}$Sr.

The various shielded and non-shielded components in the elution system play a pivotal role in providing a desired dose and ensuring that no radioisotope breakthrough occurs during the elution process. Cardiogen-82® and RUBY-FILL® are known $^{82}$Sr/$^{82}$Rb generator systems and represent system where the dose calibrator is either not included or included within the cabinet structure. There is a need for providing the dose calibrator outside the main cabinet structure and to ensure that such configurations are safe for the user and for the patient. Outside dose calibrator may advantageously remain out high dose radioactivity fields and at a stable location so as to maintain precision of its radioactivity detection.

SUMMARY

An object of the present disclosure is to provide new configurations of a $^{82}$Sr/$^{82}$Rb elution system wherein the dose calibrator is not within a main cabinet structure. Another object of the disclosure is to provide safety means that are adapted to these new configurations of a $^{82}$Sr/$^{82}$Rb elution system.

The present disclosure concerns any of the following items:

Item 1. A rubidium elution system comprising:
 a. a primary assembly including a $^{82}$Sr/$^{82}$Rb generator, an activity detector, a waste container, a pump system, a sensor, a tubing circuit, at least one valve, and a computer; and
 b. a dose calibrator that is located outside the primary assembly, and
 c. a locking means for preventing a user of the system from changing a configuration of the dose calibrator.

Item 2. The rubidium elution system of item 1, further comprising an interface for configuring the dose calibrator, and wherein the locking means prevent the user from changing a configuration the dose calibrator by locking the interface.

Item 3. The rubidium elution system of item 2, wherein the locking means comprises a compartment that encloses the interface, and the compartment is locked so as to prevent the user from accessing the interface.

Item 4. The rubidium elution system of item 3, wherein the compartment enclosing the interface is i) included in the primary assembly, ii) integrated with the dose calibrator, iii) contained in a secondary assembly that includes the dose calibrator, or iv) separated from the primary assembly and the dose calibrator.

Item 5. The rubidium elution system of any one of items 1 to 4, wherein the dose calibrator and the computer are in electronic communication.

Item 6. The rubidium elution system of item 5, wherein the electronic communication is wireless.

Item 7. The rubidium elution system of item 5, wherein the electronic communication is via a network system.

Item 8. The rubidium elution system of item 5, wherein the electronic communication is via an electronic cable.

Item 9. The rubidium elution system of item 8, wherein said electronic cable has a breakaway connector.

Item 10. The rubidium elution system of item 9, wherein the breakaway connector is a magnetic connector.

Item 11. The rubidium elution system of any one of items 1 to 10, wherein the primary assembly is positioned on a first platform, and the dose calibrator is positioned on a second platform.

Item 12. The rubidium elution system of item 11, wherein the first platform is mobile.

Item 13. The rubidium elution system of item 11 or 12, wherein the second platform is stationary.

Item 14. The rubidium elution system of any one of items 1 to 10, wherein the primary assembly and the dose calibrator are positioned on a single platform.

Item 15. The rubidium elution system of any one of items 5 to 13, wherein the computer provides a notification to a user of the system that the dose calibrator is disconnected from the computer, when the dose calibrator and the computer are disconnected from each other.

Item 16. The rubidium elution system of any one of items 5 to 13, wherein the computer provides instructions to a user of the system to connect the dose calibrator with the computer, when i) the user initiates the daily quality control, and ii) the dose calibrator and the computer are disconnected from each other.

Item 17. The rubidium elution system of any one of items 5 to 13, wherein the computer provides a notification to a user of the system that the dose calibrator is connected to the computer, when the dose calibrator and the computer are connected to each other.

Item 18. The rubidium elution system of item 11, wherein the first platform and the second platform are mobile, and the first and second platforms are removably attached together so as to permit movement of the first platform with the second platform.

Item 19. The rubidium elution system of item 11, wherein the first platform and the second platform are mobile, wherein the primary assembly is housed in a first cabinet structure, and the dose calibrator is housed or partly housed in a second cabinet structure, and the first and second cabinet structures are removably attached together so as to permit movement of the first platform with the second platform.

Item 20. The rubidium elution system of item 18 or 19, further comprising a handle for use in moving the first and second platforms together.

Item 21. The rubidium elution system of item 18, 19 or 20, wherein the first platform, the second platform, or both has wheels and a mechanism for braking and locking the wheels.

Item 22. The rubidium elution system of any one of items 1 to 21, wherein the computer is configured to control the pump and the at least one valve to provide elution of a constant activity rate of rubidium from the generator.

Item 23. The rubidium elution system of any one of items 1 to 22, wherein the $^{82}Sr/^{82}Rb$ generator, the dose calibrator, the waste container, and the activity detector are each enclosed in respective shielded compartments.

Item 24. The elution system of item 23, wherein the waste container is housed within an enclosure that may be removed from said shielded compartment.

Item 25. A rubidium elution system comprising:
  a. a primary assembly including a $^{82}Sr/^{82}Rb$ generator, an activity detector, a waste container, a pump system, a sensor, a tubing circuit, at least one valve, and a computer; wherein the primary assembly is housed in a first cabinet structure; and
  b. a dose calibrator that is located outside the first cabinet structure, wherein the dose calibrator and the computer are in electronic communication.

Item 26. The rubidium elution system of item 25, wherein the electronic communication is wireless.

Item 27. The rubidium elution system of item 25, wherein the electronic communication is via a network system.

Item 28. The rubidium elution system of item 25, wherein the electronic communication is via an electronic cable.

Item 29. The rubidium elution system of item 28, wherein the cable has a breakaway connector.

Item 30. The rubidium elution system of item 29, wherein the breakaway connector is a magnetic connector.

Item 31. The rubidium elution system of any one of items 25 to 30, wherein the system further comprises a locking means for preventing a user of the system from changing a configuration of the dose calibrator.

Item 32. The rubidium elution system of item 31, wherein the system further comprises an interface for configuring the dose calibrator, and wherein the locking means locks the interface in order to prevent the user from reconfiguring the dose calibrator.

Item 33. The rubidium elution system of item 32, wherein the locking means comprise a compartment that encloses the interface, wherein the compartment may be locked so as to prevent user from accessing the interface.

Item 34. The rubidium elution system of item 33, wherein the compartment enclosing the interface is i) included in the primary assembly, ii) integrated in the dose calibrator, iii) contained a secondary assembly that includes the dose calibrator, or iv) separated from the primary assembly and the dose calibrator.

Item 35. The rubidium elution system of any one of items 25 to 34, wherein the primary assembly is positioned on a first platform, and the dose calibrator is positioned on a second platform.

Item 36. The rubidium elution system of item 35, wherein the first platform is mobile.

Item 37. The rubidium elution system of item 35 or 36, wherein the second platform is stationary.

Item 38. The rubidium elution system of any one of items 25 to 34, wherein the primary assembly and the dose calibrator are positioned on a single platform.

Item 39. The rubidium elution system of any one of items 25 to 37, wherein the computer provides a notification to a user of the system that the dose calibrator is disconnected from the computer, when the dose calibrator and the computer are disconnected from each other.

Item 40. The rubidium elution system of any one of items 25 to 37, wherein the computer provides instructions to a user of the system to connect the dose calibrator with the computer, when i) the user initiates the daily quality control, and ii) the dose calibrator and the computer are disconnected from each other.

Item 41. The rubidium elution system of any one of items 25 to 37, wherein the computer provides a notification to a user of the system that the dose calibrator is connected to the computer, when the dose calibrator and the computer are connected to each other.

Item 42. The rubidium elution system of item 35, wherein the first platform and the second platform are mobile, and the first and second platforms are removably attached together in order to permit movement of the first platform together with the second platform.

Item 43. The rubidium elution system of item 35, wherein the first platform and the second platform are mobile, wherein the dose calibrator is housed or partly housed in a second cabinet structure, and the first and second cabinet structures are removably attached together so as to permit movement of the first platform together with the second platform.

Item 44. The rubidium elution system of item 42 or 43, further comprising a handle for use in moving the first and second platforms together.

Item 45. The rubidium elution system of any one of items 42, 43 or 44, wherein the first platform, the second platform, or both includes wheels and a mechanism for braking and locking the wheels.

Item 46. The rubidium elution system of any one of items 24 to 43, wherein the computer is configured to control the pump and the at least one valve to provide elution of a constant activity rate of rubidium from the generator.

Item 47. A rubidium elution system comprising:
  a. a primary assembly including a $^{82}Sr/^{82}Rb$ generator, an activity detector, a waste container, a pump system, a sensor, a tubing circuit, at least one valve, and a computer; wherein the primary assembly is positioned on a first platform, and the first platform is mobile; and
  b. a dose calibrator that is located outside the primary assembly, wherein the dose calibrator is positioned on a second platform, and the second platform is mobile.

Item 48. The rubidium elution system of item 47, wherein the dose calibrator and the computer are in electronic communication.

Item 49. The rubidium elution system of item 48, wherein the electronic communication is wireless.

Item 50. The rubidium elution system of item 48, wherein the electronic communication is via a network system.

Item 51. The rubidium elution system of item 48, wherein the electronic communication is via an electronic cable.

Item 52. The rubidium elution system of item 51, wherein said electronic cable has a breakaway connector.

Item 53. The rubidium elution system of item 52, wherein the breakaway connector is a magnetic connector.

Item 54. The rubidium elution system of any one of items 47 to 53, wherein the computer provides a notification to a user of the system that the dose calibrator is disconnected from the computer, when the dose calibrator and the computer are disconnected from each other.

Item 55. The rubidium elution system of any one of items 47 to 53, wherein the computer provides instructions to a user of the system to connect the dose calibrator with the computer, when i) the user initiates the daily quality control, and ii) the dose calibrator and the computer are disconnected from each other.

Item 56. The rubidium elution system of any one of items 47 to 53, wherein the computer provides a notification to a user of the system that the dose calibrator is connected to the computer, when the dose calibrator and the computer are connected to each other.

Item 57. The rubidium elution system of any one of items 47 to 56, wherein the system further comprises locking means for preventing a user of the system from changing a configuration of the dose calibrator.

Item 58. The rubidium elution system of item 57, further comprising an interface for configuring the dose calibrator, and wherein the locking means locks the interface in order to prevent the user from reconfiguring the dose calibrator.

Item 59. The rubidium elution system of item 58, wherein the locking means comprises a compartment that encloses the interface, wherein the compartment may be locked so as to prevent the user from accessing the interface.

Item 60. The rubidium elution system of item 59, wherein the compartment enclosing the interface is i) included in the primary assembly, ii) integrated in the dose calibrator, iii) contained a secondary assembly that includes the dose calibrator, or iv) separated from the primary assembly and the dose calibrator.

Item 61. The rubidium elution system of item 47, wherein the first and second platforms are removably attached together in order to permit movement of the first platform together with the second platform.

Item 62. The rubidium elution system of item 47, wherein the primary assembly is housed in a first cabinet structure, and the dose calibrator is housed or partly housed in a second cabinet structure, and the first and second cabinet structures are removably attached together in order to permit movement of the first platform together with the second platform.

Item 63. The rubidium elution system of item 61 or 62, further comprising a handle for use in moving the first and secondary assemblies together.

Item 64. The rubidium elution system of item 61, 62, or 63, wherein the first platform, the second platform, or both has wheels and a mechanism for braking and locking the wheels.

Item 65. The rubidium elution system of any one of items 47 to 64, wherein the computer is configured to control the pump and the at least one valve to provide elution of a constant activity rate of rubidium from the generator.

Item 66. The rubidium elution system of any one of items 47 to 65, wherein the $^{82}Sr/^{82}Rb$ generator, the dose calibrator, the waste container, and the activity detector are each enclosed in respective shielded compartments.

Item 67. The elution system of item 66, wherein the waste container is housed within an enclosure that may be removed from one of the shielded compartments.

Other objects, advantages and features of the present disclosure will become more apparent upon reading of the following non-restrictive description of specific embodiments thereof, given by way of examples only with reference to the accompanying drawings.

DETAILED DESCRIPTION

As used herein, the terms "elution system", "rubidium elution system" and "$^{82}Sr/^{82}Rb$ elution system" can be used interchangeably and refer to a strontium-rubidium infusion system for use in generating a radioactive solution containing rubidium-82, measuring the radioactivity in the solution generated by the system, and infusing the radioactive solution to a patient in order to perform various studies on a patient's organ, such as heart or kidney.

As used herein, the terms "cart" or "system" or "trolley" are intended to encompass a platform. Said platform can be mobile or stationary.

As used herein, the terms "primary cart" or "primary mobile cart" refer to a first cart, which can include a first cabinet structure and/or a first platform.

As used herein, the terms "secondary cart" or "secondary mobile cart" refer to a second cart, which can include a second cabinet structure and/or a second platform.

The material used for "shielding" is made up of any radiation attenuating material, including, but not limited to, depleted uranium (U), lead (Pb), tin (Sn), antimony (Sb), tungsten (W), bismuth (Bi), any other material, or any combination thereof, as long as it provides a barrier to the radioactivity of rubidium or strontium As used herein, the term "shielded component" refers to components of the system that are surrounded by a shielding material, and may refer to the generator, the dose calibrator, the activity detector, the waste container, and/or the tubing line or a part of the tubing line.

As used herein, the term "non-shielded components" refers to components of the system that are not shielded, such as the pump, the valves, the saline reservoir, the computer, the controller of the system, the interface of the dose calibrator, and/or the tubing line or a part of the tubing line.

As used herein, the term "cabinet structure" refers to an outer structure of the system that extend upward from a platform and houses an assembly. The cabinet structure may be formed of any radiation resistant material, including, but not limited to, stainless steel, injection-molded polyurethane, or any other suitable materials or combination thereof.

As used herein, the expression "locking means for preventing access to the interface by a user of the system" refers to any mechanism, system, or technology to provide security against access by a user to the interface, such as a locked compartment enclosing the interface of the dose calibrator, the requirement for input of a security code or security data (RFID, biometric, numeric, audible, or the like) for modifying the parameters of the interface, integrating the interface into the dose calibrator in such a way that the interface is rendered not accessible, or the like. In an embodiment, only the manufacturer have access to the interface of the dose calibrator. In another embodiment, no one has access to the interface. Being placed outside the primary assembly, the dose calibrator is therefore accessible and it is advantageous to prevent a user from modifying the interface parameters in order to ensure that the dose calibrator remains set properly for the rubidium elution system of the present disclosure.

As used herein, the term "electronic communication" refers to any electronic transmission or exchange of information, such as a user's commands, configuration of parameters and measurements. The electronic communication between the interface of the dose calibrator and the computer, ensures that measurements taken by the dose calibrator are transferred to the computer, and that said measurements are coordinated with the elution of the sample to be tested by the dose calibrator.

As used herein, the term "supporting accessories" refers to items such as wheels, lever, paddle, additional saline reservoir, drawer system for housing vials, and a handle for facilitating movement of the system.

The generator column may be prepared in accordance with U.S. Pat. No. 8,071,959, the entire contents of which are incorporated herein by reference.

The generator system should be able to perform all the desired functions without unwanted and hazardous effects. $^{82}$Rb has a half-life of 75 seconds, and its potential impurities, $^{82}$Sr and $^{85}$Sr, have a half-life of 25.3 days and 64.8 days, respectively. It is essential that patients are not exposed to these undesired isotopes, of which both are characterized by a long half-life. Accordingly, in order to ensure adequate safety, quality control testing of the generator is performed on daily basis prior to use. The daily quality control process for the generator includes collecting an eluted sample in a shielded vial for evaluation, and measuring the activity of the sample in a dose calibrator. Further, the sample is retained to permit decay of all active rubidium, after which a second stage of breakthrough testing is performed. The measured initial activity and the final activity are used to calculate the breakthrough information. The United States Pharmacopeia (USP) provides relevant regulatory limits for breakthrough of strontium of 0.02 µCi of $^{82}$Sr/mCi of $^{82}$Rb activity and 0.2 µCi of $^{85}$Sr/mCi of $^{82}$Rb activity. Further, to ensure a higher degree of safety, a system may impose a more stringent limit of 50% of the USP limits.

A constant activity-rate refers to an activity-rate delivered with respect to time wherein the activity-rate is constant with respect to a predetermined constant activity concentration. A method to deliver a constant activity-rate dose is described in U.S. Pat. No. 7,813,841, which is incorporated herein by reference.

Different elution strategies that can be used for patient infusions include:
  Constant-Activity elutions, which allow the user to enter the desired activity and duration of the elution. The system automatically estimates a flow rate and controls flow through the generator or a bypass line by a comparison algorithm to achieve activity around the desired set point.
  Constant-Flow elutions, which allow the user to specify the desired activity and the flow rate. The elution duration is automatically estimated based on the activity vs. volume curve measured during calibration.
  Constant-Time elutions, which allow the user to specify the desired activity and time for the elution. The flow rate is automatically calculated based on the activity vs. volume curve measured during calibration.

In an embodiment of the present disclosure, the rubidium elution system includes a controller configured to control the pump and the at least one valve so as to deliver a solution of rubidium at a constant activity rate to a patient. Said controller is preferably included in the primary assembly and carried on a first platform.

Figure 1:
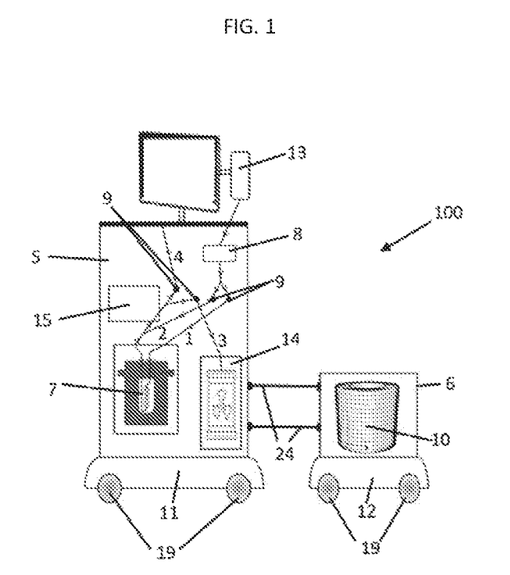
FIG. 1 illustrates an embodiment of the present disclosure wherein the generator, the waste container and the pump are carried on a mobile first platform, and the dose calibrator is carried on a mobile second platform; both platforms are removably attached to each other through a removable attachment of the cabinet structures; and the top surface of the compartment housing the waste container is lower than the top surface of the compartment housing the generator.

FIG. 1 shows a front view of a rubidium elution system according to the present disclosure. The elution system 100 comprises of two mobile platforms 11 and 12, either or both platforms 11 and 12 can be manually or motor driven. In this embodiment, each of platforms 11 and 12 has two pairs of wheels 19 mounted on a bottom side of the platforms 11 and 12, in order to allow the mobility of the system. The first cabinet structure 5 includes a front door 20 (shown in FIG. 5) that can be opened in order to access the generator 7, tubing circuit and other components. The tubing circuit includes an eluant line 1 that provides an eluant (preferably a saline solution contained in a saline reservoir 13) to the generator 7 by means of a pump 8. The tubing circuit also includes a bypass line 2 connected to the eluant line 1 that carries the eluant to the tubing circuit downstream the generator 7 such that the eluant bypasses the generator 7. The tubing circuit further includes a waste line 3 that directs into a waste container 14 a mixture composed of the eluant fed by the bypass line 2 and the radioactive eluate that has exited the generator 7. The tubing circuit also further includes a patient line 4 that directs the same mixture to either i) a patient for infusing said patient with a rubidium solution, or ii) a vial located in the dose calibrator 10 for system's calibration and strontium breakthrough test. The activity detector 15 can be a beta detector, a positron detector, or a beta and positron detector.

In certain embodiments, the pump system comprises a pump 8 that can be embodied by a syringe pump, a peristaltic pump, another type of pump, or a combination thereof.

In the embodiment, the top surface of a compartment housing the waste container 14 is lower than the top surface of the compartment housing the generator 7, as illustrated in FIG. 1. In another embodiment, the waste container can be at the same elevation than the generator 7. In a further embodiment, the top surface of a compartment housing the waste container 14 is higher than the top surface of the compartment housing the generator 7, as illustrated in FIG. 4.

Figure 2:
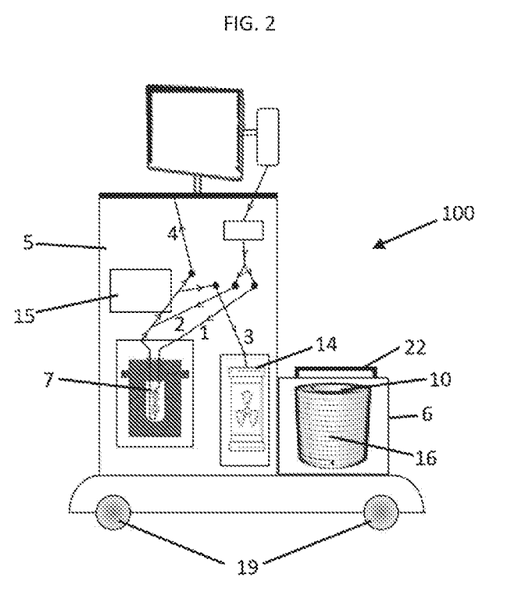
FIG. 2 illustrates an embodiment of the present disclosure wherein the generator, the pump, the waste container are housed in first cabinet structure and the dose calibrator is housed within a second cabinet structure, both cabinet structures are carried by a single mobile platform bearing two pairs of wheels.

FIG. 2 provides a front view of an embodiment of the present rubidium elution systems, wherein the rubidium elution system 100 comprises a first and a second assemblies, and each assembly is housed within a first cabinet structure 5 and a second cabinet structure 6, respectively. In this embodiment, both cabinet structures 5 and 6 are positioned on a single platform 21, which is advantageously mobile. Said platform 21 can be manually or motor driven. The platform 21 has preferably two pair of wheels 19 mounted on a bottom side of the platform 21, in order to allow mobility of the system. The second cabinet structure 6 is an optional element of this embodiment. More particularly, a variant of this embodiment is envisioned where the dose calibrator stands beside the first cabinet structure on the single platform. A handle 22 is advantageously provided for manual displacement of the system. The handle 22 can be located on the first cabinet structure 5 (not illustrated), on the second cabinet structure 6 as shown in FIG. 2, or on the platform (not illustrated).

Figure 3:
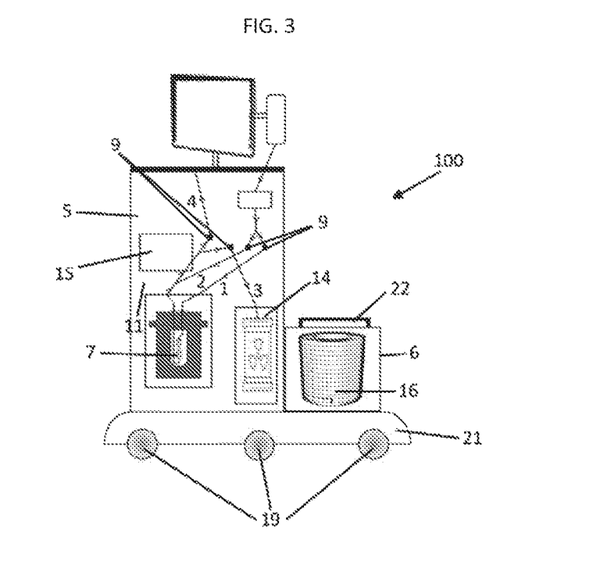
FIG. 3 illustrates an embodiment of the present disclosure similar to the embodiment shown in FIG. 2, except that the mobile platform has three pairs of wheels.

FIG. 3 provides a front view of a further embodiment of the rubidium elution 100 system of the present disclosure, where the single platform 21 has three pairs of wheels 19 that are preferably mounted on a bottom side of the platform 21.

Figure 4:
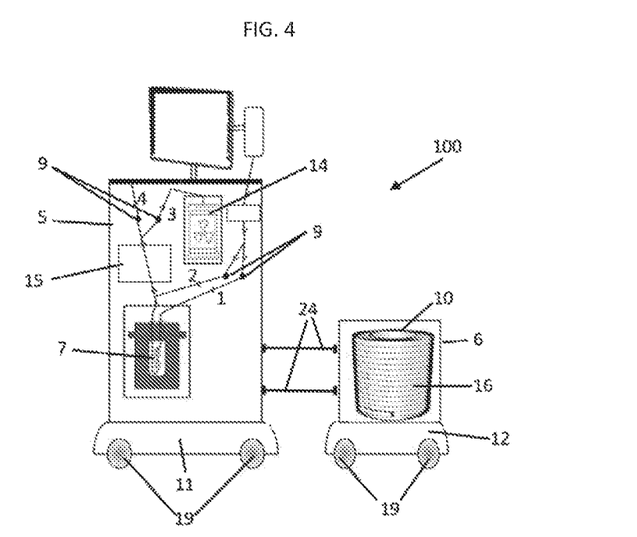
FIG. 4 illustrates an embodiment of the present disclosure that is similar to the embodiment shown in FIG. 1 with the exception that the compartment housing the waste container is higher than the compartment housing the generator.

FIG. 4 illustrates of another embodiment of the rubidium elution system 100 of the present disclosure, which includes a mobile first platform 11 and a mobile second platform 12. In this embodiment, the waste container 14 is at an elevation higher than the elevation of the generator 7. The rubidium elution system 100 of the present disclosure preferably includes and an activity detector 15 that is represented with a box for sake of simplicity in FIG. 1-4. The activity detector 15 allows the detection and measurement of the radioactivity in the tubing circuit. Preferably, the activity detector 15 is positioned downstream the generator 7 and the bypass line 2 in order to measure the radioactivity of the mixture of the radioactive eluate exiting the generator 7 with the bypassed eluant. The circulation of the fluid (eluant and eluate) in the tubing circuit is obviously ensured via the use of valves 9. Preferably, said at least one valve 9 comprises a valve upstream the generator 7 and a valve downstream the generator 7.

Figure 5:
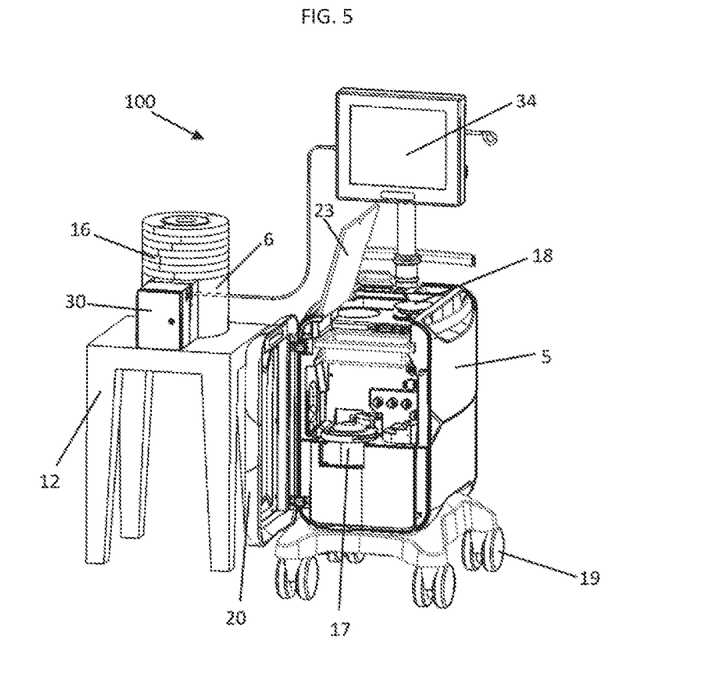
FIG. 5 illustrates an embodiment of the present disclosure wherein the generator, the waste container and the pump are carried on a mobile first platform, and the dose calibrator is positioned on a stationary second platform.

FIG. 5 provides a view of another embodiment of the present rubidium elution system 100 of the present disclosure, where the dose calibrator 10 is positioned on a stationary second platform 12. In FIG. 5, the stationary second platform 12 is embodied by a stool for sake of the illustration. However, the stationary second platform 12 can be a benchtop, a desk, a table, a kiosk, a countertop, or any other fixed location. The dose calibrator 10 and its shielded compartment are relatively heavy and there is an advantage for the user to move the rubidium elution system 100 without the dose calibrator 10. Since the dose calibrator 10 is a sensitive apparatus, positioning the dose calibrator at a fixed location represents an additional benefit of this embodiment. The dose calibrator 10 is enclosed in a shielded compartment composed of multiple rings of lead positioned on top of each other in order to form a tubular compartment upwardly opened. The illustrations of FIG. 1-5 show the pile of lead rings and it should be understood that the dose calibrator 10 is located inside these rings of lead. The lead rings provide a strong barrier to radioactivity emission from inside (the sample) and from outside (the surrounding elements containing rubidium and/or strontium). Therefore, the dose calibrator compartment composed of lead rings prevents any interference coming from the surrounding elements with the radioactivity of a sample located inside the lead rings for calibration test and/or breakthrough test.

Figure 6A:
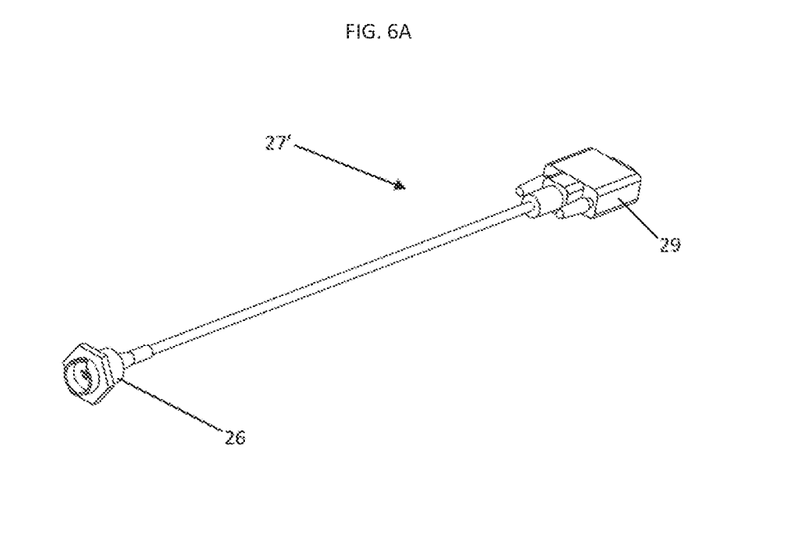
FIGS. 6A and 6B illustrate both sections of an electronic cable, where the section of the cable shown in FIG. 6A has a male portion of a magnetic connector, and the other section of the cable shown in FIG. 6B has a female portion of the magnetic connector.
Figure 6B:
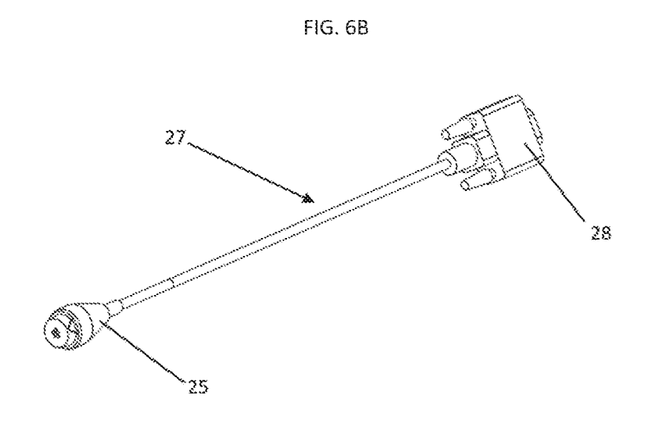

For the purpose of the breakthrough tests and calibration tests, the primary assembly is preferably placed close to or adjacent to the dose calibrator 10. The computer of the system can communicate with the dose calibrator 10 via a network (that may optionally include Wi-Fi), via a wireless connection (e.g. Bluetooth) or via a direct electronic connection (e.g. Ethernet, USB or serial cable). For the quality control and calibration tests, a sample of rubidium solution is collected in a vial that is located in the dose calibrator by means of the patient line. In a preferred embodiment, when the dose calibrator 10 is connected to the computer by an electronic cable, said cable is equipped with a breakaway connector. In a preferred embodiment, the breakaway connector is a magnetic connector. An example of a magnetic connector is the Male and Female Magnetic Connector manufactured by Rosenberger Group, Germany, which is illustrated in FIGS. 6A and 6B. More particularly, FIG. 6A shows one section 27 of the cable having the male portion 25 of the magnetic connector and a connector 28 for connecting the interface. FIG. 6B shows the other section 27' of the cable having the female portion 26 of the magnetic connector and a connector 29 for connecting the computer. It should be understood that the present disclosure encompasses other types of breakaway connector that have the ability to detach when the primary assembly is moved away from the dose calibrator. When the cable 27 is connected to the dose calibrator 10 through an interface, said interface is preferably solidly attached to the dose calibrator so that pulling on the cable section 27' results in disconnecting both portions 25 and 26 of the breakaway connector.

In certain embodiments, the first and second platforms 11 and 12 are mobile and are removably attached to each other. The attachment 24 can be achieved through the attachment 24 of the cabinet structures 5 and 6 (indirect attachment as represented in FIGS. 1 and 4) or the attachment can be achieved by the attachment of the platforms 11 and 12 together (direct attachment—not shown). The removable attachment 24 is schematically represented by two solid lines in FIGS. 1 and 4. For the purpose of this embodiment, any removable attaching means known by a skilled technician can be used. In an embodiment, the dose calibrator is housed in a second cabinet structure 6. In another embodiment, the dose calibrator is partially housed in a second cabinet structure. In further embodiment, there is no second cabinet structure housing the dose calibrator. In an embodiment, the first and second cabinet structures 5 and 6 are removably attached together so as to move the first and second platforms together. In alternate embodiment, the first and second cabinet structures 5 and 6 can be moved independently from each other. In this embodiment, the attachments 24 preferably provide sufficient flexibility to move the cabinet structures 5 and 6 independently from each other.

In some embodiments, the $^{82}$Sr/$^{82}$Rb generator, the dose calibrator, the waste container, and the activity detector are each enclosed within respective shielded compartments. Preferably, each of the $^{82}$Sr/$^{82}$Rb generator, the dose calibrator, the waste container, and the activity detector is enclosed within respective shielded compartments. The door 31 of the waste compartment 18 is preferably shielded. The opening of the generator is also preferably shielded.

In another aspect, the second platform 12 include an optional storage compartment, such as a space, tray, drawer, or bin for carrying one or more additional components. Such additional components may include supplies that can include, but are not limited to, tubing for the dose calibrator, vials for the dose calibrator, and other related medical supplies.

Figure 8:
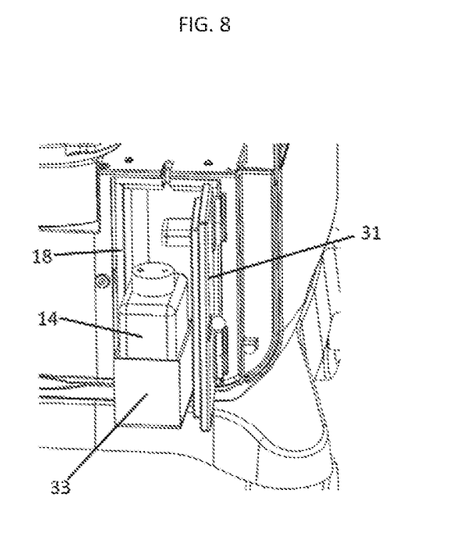
FIG. 8 is a close-up view of an embodiment of the compartment housing the waste container where the door of the compartment is opened and the waste container is housed within an enclosure that may be removed from its compartment.

In another aspect, the waste container 14 is housed within an enclosure (shown in FIG. 8) that may be removed from its shielded compartment 18. In embodiments, the waste container compartment 18 can be accessed by opening a side door 20 of the first cabinet structure 5 in the configurations of FIG. 1-4, or by opening a top panel 23 of the first cabinet structure 5 as shown in FIG. 5. In a certain embodiment, the waste container 14 can be accessed from the waste container compartment 18 horizontally by mounting a waste platform on rails. In this embodiment, the waste platform is slid out horizontally prior to pulling out the waste container 14 from its compartment. In another compartment, the waste container 14 is removed by a lifting mechanism that can be automated.

In certain embodiments, at least one of the first and second platforms 11 and 12 includes wheels for allowing the mobility thereof, and a mechanism for braking and locking the wheels, such as a lever.

In other aspects, the computer of the rubidium elution system is configured to proceed with a quality control test (breakthrough tests) at pre-determined time, upon user's request and at least once a day. The computer is configured to prevent a patient infusion when the quality control test result determines that the strontium concentration is equal to or above 0.01 µCi of $^{82}$Sr/mCi of $^{82}$Rb activity or equal to or above 0.1 µCi of $^{85}$Sr/mCi of $^{82}$Rb activity.

Figure 7:
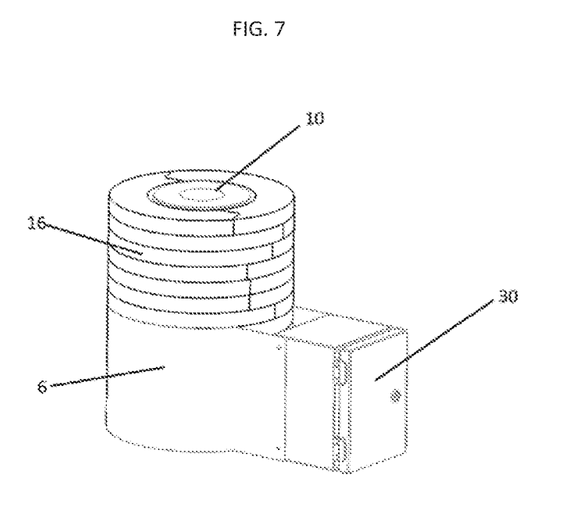
FIG. 7 illustrates a compartment enclosing the interface of a dose calibrator that is adjacent to the dose calibrator.

In accordance with the presently disclosed subject matter, the dose calibrator 10 is outside the primary assembly. The present disclosure includes embodiments where the dose calibrator is accompanied with its own interface that configures the dose calibrator for detection of rubidium, and with embodiments where the calibrator has no interface and is controlled by the computer. When the dose calibrator is accompanied with its own interface, said interface may be accessible to a user and therefore, there is a need for preventing a user from reconfiguring the interface of the dose calibrator 10. As such, in certain preferred embodiments, the system further includes a locking means for preventing a user from reconfiguring the dose calibrator in such a way that the dose calibrator remains configured as initially configured by the manufacturer. In a preferred embodiment, the dose calibrator is configured to detect rubidium and/or strontium. In a further preferred embodiment, the dose calibrator is configured to detect rubidium. Since strontium and rubidium are in an instant equilibrium, one can use the measured quantity of rubidium to calculate the quantity of strontium that is present in a solution after the initial content in rubidium has decayed. On way to prevent a user from reconfiguring the dose calibrator is to prevent access to the interface of the dose calibrator. In an embodiment, the locking means comprises an identification system for allowing access to the interface and reconfiguring the dose calibrator by the manufacturer of the system and not the user of the system. In another embodiment, the locking means comprises a locked compartment 30 as shown in FIGS. 5 and 7, which encloses the interface of the dose calibrator 10 and prevents access to by the user of the system. Preferably, the manufacturer of the system remains able to unlock the compartment of the interface and able to configure or reconfigure the dose calibrator as needed. In a variant of this embodiment, the locked compartment enclosing the interface of the dose calibrator 10 is provided by a second cabinet structure 6 that also encloses or partly encloses the dose calibrator 10. The compartment enclosing the interface can be i) included in the primary assembly, ii) integrated in the dose calibrator, iii) contained a secondary assembly that includes the dose calibrator, or iv) separated from the primary assembly and the dose calibrator. In a further embodiment, there is no interface, and the computer does not allow the user to modify the configurations of the dose calibrator.

In another aspect of the present disclosure, the rubidium elution system 100 comprises a computer screen 34 (shown in FIG. 5) includes a speaker for providing an audible or visible alert for one or more different operations of system.

In another aspect of the present disclosure, the rubidium elution system 100 comprises a computer that comprises a processor, and a memory communicatively connected to the processor when the system is functioning, as well as processor-executable instructions, that, when executed on the processor, cause the system to perform representative functions of the system. Additionally, certain embodiments may be implemented as computer-executable instructions stored on computer-readable storage media. Computer readable storage media may be distinguished from computer-readable communications media that include transitory signals.

While the presently disclosed subject matter has been described in detail with reference to certain preferred embodiments, it should be appreciated that the present disclosure is not limited to those precise embodiments. Rather, in view of the present disclosure, which describes the current best mode for practicing the disclosed embodiments, many modifications and variations would present themselves to those skilled in the art without departing from the scope, and spirit of the presently disclosed subject matter.

What is claimed is:

1. A rubidium elution system comprising:
   a. a primary assembly including a $^{82}$Sr/$^{82}$Rb generator, an activity detector, a waste container, a pump system, a sensor, a tubing circuit, at least one valve, and a computer; wherein the primary assembly is housed in a first cabinet structure; and
   b. a dose calibrator that is located outside the first cabinet structure, wherein the dose calibrator and the computer are in electronic communication,
   wherein the primary assembly is positioned on a first platform, and the dose calibrator is positioned on a second platform.

2. The rubidium elution system of claim 1, wherein the electronic communication is wireless.

3. The rubidium elution system of claim 1, wherein the electronic communication is via a network system.

4. The rubidium elution system of claim 1, wherein the electronic communication is via an electronic cable.

5. The rubidium elution system of claim 4, wherein the cable has a breakaway connector.

6. The rubidium elution system of claim 5, wherein the breakaway connector is a magnetic connector.

7. The rubidium elution system of claim 1, wherein the system further comprises a locking means for preventing a user of the system from changing a configuration of the dose calibrator.

8. The rubidium elution system of claim 7, wherein the system further comprises an interface for configuring the dose calibrator, and wherein the locking means locks the interface in order to prevent the user from reconfiguring the dose calibrator.

9. The rubidium elution system of claim 8, wherein the locking means comprise a compartment that encloses the interface, wherein the compartment may be locked so as to prevent user from accessing to the interface.

10. The rubidium elution system of claim 9, wherein the compartment enclosing the interface is i) included in the primary assembly, ii) integrated in the dose calibrator, iii) contained a secondary assembly that includes the dose calibrator, or iv) separated from the primary assembly and the dose calibrator.

11. The rubidium elution system of claim 1, wherein the first platform is mobile.

12. The rubidium elution system of claim 1, wherein the second platform is stationary.

13. The rubidium elution system of claim 1, wherein the primary assembly and the dose calibrator are positioned on a single platform.

14. The rubidium elution system of claim 1, wherein the computer provides a notification to a user of the system that the dose calibrator is disconnected from the computer, when the dose calibrator and the computer are disconnected from each other.

15. The rubidium elution system of claim 1, wherein the computer provides instructions to a user of the system to connect the dose calibrator with the computer, when i) the user initiates the daily quality control, and ii) the dose calibrator and the computer are disconnected from each other.

16. The rubidium elution system of claim 1, wherein the computer provides a notification to a user of the system that the dose calibrator is connected to the computer, when the dose calibrator and the computer a connected to each other.

17. The rubidium elution system of claim 1, wherein the first platform and the second platform are mobile, and the first and second platforms are removably attached together in order to permit movement of the first platform tog r with the second platform.

18. The rubidium elution system of claim 1, wherein the first platform and the second platform are mobile, wherein the dose calibrator is housed or partly housed in a second cabinet structure, and the first and second cabinet structures are removably attached together so as to permit movement of the first platform together with the second platform.

19. A rubidium elution system comprising:
   a. a primary assembly including a $^{82}$Sr/$^{82}$Rb generator, an activity detector, a waste container, a pump system, a sensor, a tubing circuit, at least one valve, and a computer; wherein the primary assembly is housed in a first cabinet structure; and
   b. a dose calibrator that is located outside the first cabinet structure, wherein the dose calibrator and the computer are in electronic communication, wherein the computer provides a notification to a user of the system that the dose calibrator is disconnected from the computer, when the dose calibrator and the computer are disconnected from each other.

20. A rubidium elution system comprising:
   a. a primary assembly including a $^{82}$Sr/$^{82}$Rb generator, an activity detector, a waste container, a pump system, a sensor, a tubing circuit, at least one valve, and a computer; wherein the primary assembly is housed in a first cabinet structure; and
   b. a dose calibrator that is located outside the first cabinet structure, wherein the dose calibrator and the computer are in electronic communication, wherein the computer provides instructions to a user of the system to connect the dose calibrator with the computer, when i) the user initiates the daily quality control, and ii) the dose calibrator and the computer are disconnected from each other.

21. A rubidium elution system comprising:
   a. a primary assembly including a $^{82}$Sr/$^{82}$Rb generator, an activity detector, a waste container, a pump system, a sensor, a tubing circuit, at least one valve, and a computer; wherein the primary assembly is housed in a first cabinet structure; and
   b. a dose calibrator that is located outside the first cabinet structure, wherein the dose calibrator and the computer are in electronic communication, wherein the computer provides a notification to a user of the system that the dose calibrator is connected to the computer, when the dose calibrator and the computer are connected to each other.

\* \* \* \* \*